United States Patent
Elomari et al.

(10) Patent No.: US 7,576,252 B2
(45) Date of Patent: *Aug. 18, 2009

(54) PROCESS FOR THE FORMATION OF A SUPERIOR LUBRICANT OR FUEL BLENDSTOCK BY IONIC LIQUID OLIGOMERIZATION OF OLEFINS IN THE PRESENCE OF ISOPARAFFINS

(75) Inventors: Saleh Elomari, Fairfield, CA (US); Russell Krug, Novato, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 577 days.

This patent is subject to a terminal disclaimer.

(21) Appl. No.: 11/316,628

(22) Filed: Dec. 20, 2005

(65) Prior Publication Data

US 2007/0142691 A1   Jun. 21, 2007

(51) Int. Cl.
*C07C 2/62* (2006.01)

(52) U.S. Cl. .................... 585/722; 585/727; 585/728

(58) Field of Classification Search .............. 585/722, 585/727, 728

See application file for complete search history.

(56) References Cited

U.S. PATENT DOCUMENTS

| | | | |
|---|---|---|---|
| 5,750,455 | A | 5/1998 | Chauvin et al. |
| 6,028,024 | A | 2/2000 | Hirschauer et al. |
| 6,395,948 | B1 | 5/2002 | Hope et al. |
| 2001/0001804 | A1 | 5/2001 | Skledar et al. |

FOREIGN PATENT DOCUMENTS

EP    0 791 643    8/1997

*Primary Examiner*—Thuan Dinh Dang
(74) *Attorney, Agent, or Firm*—Susan M. Abernathy; David M. Tuck

(57) ABSTRACT

A process and method for making a superior lubricant or distillate fuel component by the oligomerization/alkylation of a mixture comprising olefins and isoparaffins to produce an alkylated ("capped") olefin oligomer using an acidic chloroaluminate ionic liquid catalyst system. Preferably the ionic liquid catalyst system comprises a Brönsted acid.

18 Claims, No Drawings

PROCESS FOR THE FORMATION OF A SUPERIOR LUBRICANT OR FUEL BLENDSTOCK BY IONIC LIQUID OLIGOMERIZATION OF OLEFINS IN THE PRESENCE OF ISOPARAFFINS

BACKGROUND OF THE INVENTION

Olefin oligomers and relatively long chain olefins can be used in the production of fuel and lubricant components or blendstocks. One problem with the use of olefins in either of the above uses is that the olefinic double bond can be undesirable. Olefinic double bonds cause problems in both fuels and in lubricants. Olefins can oligomerize forming 'gum' deposits in the fuel. Olefins in fuel are also associated with air quality problems. Olefins can also oxidize which can be a particular problem in lubricants. One way of minimizing the problem is to hydrogenate some or all of the double bonds to form saturated hydrocarbons. A method of doing this is described in US published Application US 2001/0001804 which is incorporated herein in its entirety. Hydrogenation can be an effective way to minimize the concentration of olefins in the lubricant or fuel however it requires the presence of hydrogen and a hydrogenation catalyst both of which can be expensive. Also excessive hydrogenation can lead to hydrocracking. Hydrocracking can increase as one attempts to hydrogenate the olefins to increasingly lower concentrations. Hydrocracking is generally undesirable as it produces a lower molecular weight material where the goal in oligomerization is to produce a higher molecular weight material. Directionally it would generally be preferred to increase, not decrease the average molecular weight of the material. Thus using the hydrogenation method it is desired to hydrogenate the olefins as deeply as possible while minimizing any hydrocracking or hydrodealkylation. This is inherently difficult and tends to be a compromise.

Hydrocracking of a slightly branched hydrocarbon material can also lead to less branching. Cracking tend to be favored at the tertiary and secondary centers. For example a branched hydrocarbon can crack at a secondary center forming two more linear molecules which is also directionally undesirable.

Potentially, Ionic Liquid catalyst systems can be used for the oligomerization of olefins such as normal alpha olefins to make olefin oligomers. A Patent that describes the use of an ionic liquid catalyst to make polyalphaolefins is U.S. Pat. No. 6,395,948 which is incorporated herein by reference in its entirety. A published application that discloses a process for oligomerization of alpha olefins in ionic liquids is EP 791,643.

Ionic Liquid catalyst systems have also been used for isoparaffins-olefins alkylation reactions. Patents that disclose a process for the alkylation of isoparaffins by olefins are U.S. Pat. Nos. 5,750,455 and 6,028,024.

It would be desirable to have a process for making a lubricant or distillate fuel starting materials with low degree of unsaturation (low concentration of double bonds) and thus reducing the need for deep hydrogenation while preferably maintaining or more preferably increasing the average molecular weight and branching of the material. The present invention provides a new process with just such desired features.

SUMMARY OF THE INVENTION

The present invention provides a process for making a fuel or lubricant component by the oligomerization of olefins to make olefin oligomers of desired chain length range by alkylation of the olefin oligomer with an isoparaffin to "cap" at least a portion of the remaining double bonds of the olefin oligomers.

A particular embodiment of the present invention provides a process for making a distillate fuel component or lubricant component, comprising, contacting a stream comprising one or more olefins and a stream comprising one or more isoparaffins with a catalyst comprising an acidic chloroaluminate ionic liquid in the presence of a Brönsted acid to form an alkylated oligomeric product having a Bromine Number of less than 4.

In another embodiment of the present invention, a process is disclosed for making a fuel or lubricant, comprising, passing a mixture comprising olefins and an isoparaffin to an oligomerization/alkylation zone comprising an acidic chloroaluminate ionic liquid, at oligomerization/alkylation conditions to form a alkylated oligomeric product having a TBP@50 of at least 1000 degrees by Simulated Distillation (SIMDIST) and a Bromine Number of less than 4.

Oligomerization of two or more olefin molecules results in the formation of an olefin oligomer that generally comprises a long branched chain molecule with one remaining double bond. The present invention provides a novel way to reduce the concentration of double bonds and at the same time enhance the quality of the desired fuel or lubricant. This invention also reduces the amount of hydrofinishing that is needed to achieve a desired product with low olefin concentration. The olefin concentration can be determined by Bromine Index or Bromine Number. Bromine Number can be determined by test ASTM D 1159. Bromine Index can be determined by ASTM D 2710. Test methods D 1159 and ASTM D 2710 are incorporated herein by reference in their entirety. Bromine Index is effectively the number of milligrams of Bromine ($Br_2$) that react with 100 grams of sample under the conditions of the test. Bromine Number is effectively the number of grams of bromine that will react with 100 grams of specimen under the conditions of the test.

In the present Application, distillation data was generated for several of the products by Simulated Distillation (SIMDIST). Simulated Distillation (SIMDIST) involves the use of ASTM D 6352 or ASTM D 2887 as appropriate. ASTM D 6352 and ASTM D 2887 are incorporated herein by reference in their entirety. Distillation curves can also be generated using ASTM D86 which is incorporated herein by reference in its entirety.

In a preferred embodiment of the present invention HCl or a component that supplies protons is added to the reaction mixture. Although not wishing to be limited by theory, it is believed that the presence of a Brönsted acid such as HCl greatly enhances the activity and acidity of the ionic liquid catalyst system.

Among other factors, the present invention involves a surprising new way of making a lubricant base oil or fuel blendstock that has reduced levels of olefins without hydrogenation or with minimal hydrofinishing. The present invention also increases the value of the resultant olefin oligomers by increasing the molecular weight of the oligomer and increasing the branching by incorporation of isoparaffin groups into the oligomers skeletons. These properties can both add significant value to the product particularly when starting with a highly linear hydrocarbon such as the preferred feeds to the present invention (i.e. Fischer-Tropsch derived hydrocarbons). The present invention is based on the use of an acidic chloroaluminate ionic liquid catalyst to alkylate an olefin or oligomerized olefin with an isoparaffin under relatively mild conditions. Surprisingly, the alkylation can occur under effectively the same conditions as the oligomerization. Preferably the alkylation and oligomerization reactions occur together in a common reaction zone resulting in an alkylated oligomer having desirable properties.

A preferred catalyst system of the present invention is an acidic chloroaluminate ionic liquid system. More preferably the acidic chloroaluminate ionic liquid system is used in the presence of a Brönsted acid. Preferably the Brönsted acid is a halohalide and most preferably is HCl.

DETAILED DESCRIPTION OF THE INVENTION

The present invention provides a novel process for the production of fuel or lubricant components by the acid catalyzed oligomerization of olefins and alkylation with isoparaffins in ionic liquid medium to form a product having greatly reduced olefin content and improved quality. Amazingly, we found that oligomerization of an olefin and alkylation of an olefin and/or its oligomers with an isoparaffin can be performed together in a single reaction zone. The alkylated or partially alkylated oligomer stream that results has very desirable properties for use as a fuel or lubricant blendstock. In particular the present invention provides a process for making a distillate fuel, lubricant, distillate fuel component, lubricant component, or solvent having improved properties such as increased branched, higher molecular weight, and lower Bromine Number.

Ionic Liquids

Ionic liquids are a category of compounds which are made up entirely of ions and are generally a liquid at or below process temperatures. Often salts which are composed entirely of ions are solids with high melting points, for example, above 450 degrees C. These solids are commonly known as 'molten salts' when heated to above their melting points. Sodium chloride, for example, is a common 'molten salt', with a melting point of 800 degree C. Ionic liquids differ from 'molten salts', in that they have low melting points, for example, from −100 degrees C. to 200 degree C. Ionic liquids tend to be liquids over a very wide temperature range, with some having a liquid range of up to 300 degrees C. or higher. Ionic liquids are generally non-volatile, with effectively no vapor pressure. Many are air and water stable, and can be good solvents for a wide variety of inorganic, organic, and polymeric materials.

The properties of ionic liquids can be tailored by varying the cation and anion pairing. Ionic liquids and some of their commercial applications are described, for example, in J. Chem. Tech. Biotechnol, 68:351-356 (1997); J. Phys. Condensed Matter, 5:(supp 34B):B99-B106 (1993); Chemical and Engineering News, Mar. 30, 1998, 32-37; J. Mater. Chem., *:2627-2636 (1998); and Chem. Rev., 99:2071-2084 (1999), the contents of which are hereby incorporated by reference.

Many ionic liquids are amine-based. Among the most common ionic liquids are those formed by reacting a nitrogen-containing heterocyclic ring (cyclic amines), preferably nitrogen-containing aromatic rings (aromatic amines), with an alkylating agent (for example, an alkyl halide) to form a quaternary ammonium salt, and performing ion exchange or other suitable reactions with various Lewis acids or their conjugate bases to form ionic liquids. Examples of suitable heteroaromatic rings include pyridine and its derivatives, imidazole and its derivatives, and pyrrole and its derivatives. These rings can be alkylated with varying alkylating agents to incorporate a broad range of alkyl groups on the nitrogen including straight, branched or cyclic $C_{1-20}$ alkyl group, but preferably $C_{1-12}$ alkyl groups since alkyl groups larger than $C_1$-$C_{12}$ may produce undesirable solid products rather than ionic liquids. Pyridinium and imidazolium-based ionic liquids are perhaps the most commonly used ionic liquids. Other amine-based ionic liquids including cyclic and non-cyclic quaternary ammonium salts are frequently used. Phosphonium and sulphonium-based ionic liquids have also been used.

Counter anions which have been used include chloroaluminate, bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, antimony hexafluoride, copper dichloride anion, zinc trichloride anion, as well as various lanthanum, potassium, lithium, nickel, cobalt, manganese, and other metal ions. The ionic liquids used in the present invention are preferably acidic haloaluminates and preferably chloroaluminates.

The form of the cation in the ionic liquid in the present invention can be selected from the group consisting of pyridiniums, and imidazoliums. Cations that have been found to be particularly useful in the process of the present invention include pyridiniums.

Preferred ionic liquids that can be used in the process of the present invention include acidic chloroaluminate ionic liquids. Preferred ionic liquids used in the present invention are acidic pyridinium chloroaluminates. More preferred ionic liquids useful in the process of the present invention are alkyl-pyridinium chloroaluminates. Still more preferred ionic liquids useful in the process of the present invention are alkyl-pyridinium chloroaluminates having a single linear alkyl group of 1 to 6 carbon atoms in length. One particular ionic liquid that has proven effective is 1-butyl-pyridinium chloroaluminate.

In a more preferred embodiment of the present invention 1-butyl-pyridnium chloroaluminate is used in the presence of Brönsted acid. Not to be limited by theory, the Brönsted acid acts as a promoter or co-catalyst. Examples of Brönsted acids are Sulfuric, HCl, HBr, HF, Phosphoric, HI, etc. Other strong acids that are proton donors can also be suitable Brönsted acids.

The Feeds

In the process of the present invention one of the important feedstocks comprises an olefinic hydrocarbon. The olefinic group provides the reactive site for the oligomerization reaction as well as the alkylation reaction. The olefinic hydrocarbon can be a fairly pure olefinic hydrocarbon cut or can be a mixture of hydrocarbons having different chain lengths thus a wide boiling range. The olefinic hydrocarbon can be terminal olefin (an alpha olefin) or can be internal olefin (internal double bond). The olefinic hydrocarbon chain can be either straight chain or branched or a mixture of both. The feedstocks useable in the present invention can include unreactive diluents such as normal paraffins.

In one embodiment of the present invention, the olefinic feed comprises a mixture of mostly linear olefins from $C_2$ to about $C_{30}$. The olefins are mostly but not entirely alpha olefins.

In another embodiment of the present invention, the olefinic feed can comprise at least 50% of a single alpha olefin species.

In another embodiment of the present invention, the olefinic feed can be comprised of an NAO cut from a high purity Normal Alpha Olefin (NAO) process made by ethylene oligomerization.

In an embodiment of the present invention some or all of the olefinic feed to the process of the present invention comprises thermally cracked hydrocarbons, preferably cracked wax, more preferably cracked wax from a Fischer-Tropsch (FT) process. A process for making olefins by cracking FT products is disclosed in U.S. Pat. No. 6,497,812 which is incorporated herein by reference in its entirety.

In the process of the present invention, another important feedstock is an isoparaffin. The simplest isoparaffin is isobutane. Isopentanes, isohexanes, isoheptanes, and other higher isoparaffins are also useable in the process of the present invention. Economics and availability are the main drivers of the isoparaffins selection. Lighter isoparaffins tend to be less expensive and more available due to their low gasoline blend value (due to their relatively high vapor pressure). Mixtures of light isoparaffins can also be used in the present invention. Mixtures such as $C_4$-$C_5$ isoparaffins can be used and may be advantaged because of reduced separation costs. The isoparaffins feed stream may also contain diluents such as normal paraffins. This can be a cost savings by reducing the cost of separating isoparaffins from close boiling paraffins. Normal paraffins will tend to be unreactive diluents in the process of the present invention.

In an optional embodiment of the present invention the resultant alkylated oligomer made in the present invention can be hydrogenated to further decrease the concentration of olefins and thus the Bromine Number. After hydrogenation the lubricant component or base oil has a Bromine Number of less than 0.8, preferably less than 0.5, more preferably less than 0.3, still more preferably less than 0.2.

Oligomerization/Alkylation conditions for the process of the present invention include a temperature of from about 0 to about 200 degrees C., preferably from about 0 to about 150 degrees C., more preferably from about 0 to about 100, and most preferably from 20 to 70 degrees C.

In summary, the potential benefits of the process of the present invention include:
Reduced capital cost for hydrotreating/hydrofinishing
Lower operating cost due to reduced hydrogen and extensive hydrogenation requirements
Use of the same ionic liquid catalyst system for oligomerization and alkylation in one step process
Improved branching characteristics of the product
Increased overall molecular weight of the product
Incorporation of low cost feed (isoparaffins) to increase liquid yield of high value distillate fuel or lubricant components

EXAMPLES

Example 1

Preparation of Fresh 1-Butyl-pyridinium Chloroaluminate Ionic Liquid 1-butyl-pyridinium chloroaluminate is a room temperature ionic liquid prepared by mixing neat 1-butyl-pyridinium chloride (a solid) with neat solid aluminum trichloride in an inert atmosphere. The syntheses of 1-butyl-pyridinium chloride and the corresponding 1-butyl-pyridinium chloroaluminate are described below. In a 2-L Teflon-lined autoclave, 400 gm (5.05 mol.) anhydrous pyridine (99.9% pure purchased from Aldrich) were mixed with 650 gm (7 mol.) 1-chlorobutane (99.5% pure purchased from Aldrich). The neat mixture was sealed and let to stir at 125° C. under autogenic pressure over night. After cooling off the autoclave and venting it, the reaction mix was diluted and dissolved in chloroform and transferred to a three liter round bottom flask. Concentration of the reaction mixture at reduced pressure on a rotary evaporator (in a hot water bath) to remove excess chloride, unreacted pyridine and the chloroform solvent gave a tan solid product. Purification of the product was done by dissolving the obtained solids in hot acetone and precipitating the pure product through cooling and addition of diethyl ether. Filtering and drying under vacuum and heat on a rotary evaporator gave 750 gm (88% yields) of the desired product as an off-white shinny solid. $^1$H-NMR and $^{13}$C-NMR were ideal for the desired 1-butyl-pyridinium chloride and no presence of impurities was observed by NMR analysis.

1-Butyl-pyridinium chloroaluminate was prepared by slowly mixing dried 1-butyl-pyridinium chloride and anhydrous aluminum chloride ($AlCl_3$) according to the following procedure. The 1-butyl-pyridinium chloride (prepared as described above) was dried under vacuum at 80° C. for 48 hours to get rid of residual water (1-butyl-pyridinium chloride is hydroscopic and readily absorbs water from exposure to air). Five hundred grams (2.91 mol.) of the dried 1-butyl-pyridinium chloride were transferred to a 2-Liter beaker in a nitrogen atmosphere in a glove box. Then, 777.4 gm (5.83 mol.) of anhydrous powdered $AlCl_3$ (99.99% from Aldrich) were added in small portions (while stirring) to control the temperature of the highly exothermic reaction. Once all the $AlCl_3$ was added, the resulting amber-looking liquid was left to gently stir overnight in the glove box. The liquid was then filtered to remove any un-dissolved $AlCl_3$. The resulting acidic 1-butyl-pyridinium chloroaluminate was used as the catalyst for the Examples in the Present Application.

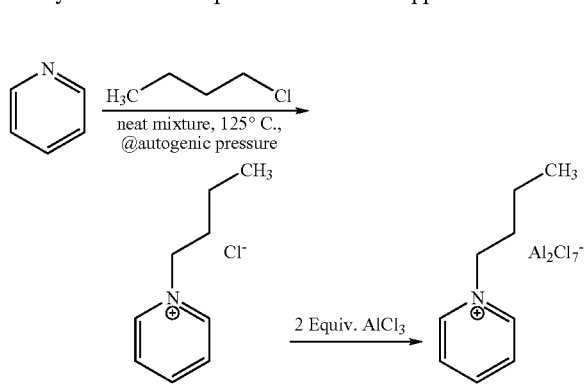

Example 2

Oligomerization of 1-Decene in Ionic Liquids in the Present of iso-Butane

Oligomerization of 1-decene was carried out in acidic 1-butyl-pyridinium chloroaluminate in the presence of 10 mole % of isobutane. The reaction was done in the presence of HCl as a promoter. The procedure below describes, in general, the process. To 42 gm of 1-butyl-pyridinium chloroaluminate in a 300 cc autoclave fitted to an overhead stirrer, 101 gm of 1-decene and 4.6 gm of isobutane were added and the autoclave was sealed. Then 0.4 gm of HCl was introduced and the stirring started. The reaction was heated to 50° C. The reaction was exothermic and the temperature quickly jumped to 88° C. The temperature in few minutes went back down to 44° C. and was brought up to 50° C. and the reaction was vigorously stirred at about 1200 rpm for an hour at the autogenic pressure (~atmospheric pressure in this case). Then, the stirring was stopped and the reaction was cooled to room temperature. The contents were allowed to settle and the organic layer (immiscible in the ionic liquid) was decanted off and washed with 0.1N KOH aqueous solution. The colorless oil was analyzed with simulated distillation and bromine analysis. The Bromine Number was 2.6. The Bromine Number is much less than that usually observed for the 1-decene oligomerization in the absence of isobutane. The Bromine Number for 1-decene oligomerization in the absence of $iC_4$ is in the range of 7.5-7.9 based on the catalyst, contact time and catalyst amounts used in the oligomerization reaction.

Table 1 compares the Bromine Numbers of the starting 1-decene, 1-decene oligomerization products in the presence of $iC_4$, 1-decene oligomerization products without $iC_4$, and the alkylation products of 1-decene oligomers with excess $iC_4$.

TABLE 1

| Material | 1-Decene | Oligomerization-alkylation of 1-Decene with 10 mol % $iC_4$ | Oligomerization Products of 1-Decene/No $iC_4$ | Alkylated 1-decene oligomers |
|---|---|---|---|---|
| Bromine Number | 114 | 2.6 | 7.9 | 2.8 |

The data above suggests that the in situ oligomerization/alkylation (where isoparaffins are introduced into the oligomerization reactor) leads to oils with low olefin concentration. The data in Table 1 compares the olefinicity of the products from in situ oligomerization/alkylation products with pure oligomers and with the products obtained from alkylating the oligomers with isobutane in a second step reaction.

Example 3

Oligomerization of a Mixture of Alpha Olefins in the Presence of Iso-Butane

A 1:1:1 mixture of 1-hexene:1-octene:1-decene was oligomerised in the presence of isobutane at the reaction conditions described earlier for oligomerization of 1-decene in the presence of isobutane (100 gm olefins, 20 gm IL catalyst, 0.25 gm HCl as co-catalyst, 50° C., autogenic pressure, 1 hr). The products were separated from the IL catalyst, and the IL layer was rinsed with hexane, which was decanted off and added to the products. The products and the hexane wash were treated with 0.1N NaOH to remove any residual $AlCl_3$. The organic layers were collected and dried over anhydrous $MgSO_4$. Concentration (on a rotary evaporator at reduced pressure, in a water bath at ~70 degrees C.) gave the oligomeric product as viscous yellow oils. Table 2 below shows the Simulated Distillation, viscosity, and pour point and cloud point data of the alkylated oligomeric products of the olefinic mixture in the presence of isobutane.

TABLE 2

| | Oligomers of $C_6^=, C_8^=, C_{10}^=$ W/$iC_4$ ° F. |
|---|---|
| SIMDIST TBP (WT %), | |
| TBP @ 0.5 | 313 |
| TBP @ 5 | 450 |
| TBP @ 10 | 599 |
| TBP @ 15 | 734 |
| TBP @ 20 | 831 |
| TBP @ 30 | 953 |
| TBP @ 40 | 1033 |
| TBP @ 50 | 1096 |
| TBP @ 60 | 1157 |
| TBP @ 70 | 1220 |
| TBP @ 80 | 1284 |
| TBP @ 90 | 1332 |
| TBP @ 95 | 1357 |
| TBP @ 99.5 | 1384 |
| Physical Properties: | |
| VI | 140 |
| VIS @ 100 | 7.34 CST |
| VIS @ 40 | 42 CST |
| Pour Point | −54° C. |
| Cloud Point | <−52° C. |
| Bromine # | 3.1 |

Example 4

Oligomerization of 1-Decene in Ionic Liquids in the Presence of Varying Iso-Butane Concentrations Oligomerization of 1-decene was carried out in acidic 1-butyl-pyridinium chloroaluminate in the presence of varying mole % of isobutane. The reaction was done in the presence of HCl as a promoter (co-catalyst). The procedure below describes, in general, the process. To 42 gm of 1-butyl-pyridinium chloroaluminate in a 300 cc autoclave fitted to an overhead stirrer, 101 gm of 1-decene and 4.6 gm of isobutane were added and the autoclave was sealed. Then 0.2-0.5 gm of HCl was introduced into the reactor, and then, started the stirring. The reaction is exothermic and the temperature quickly jumped to 88° C. The temperature dropped down quickly to the mid 40s and was brought up to 50° C. and kept at around 50° C. for the remainder of the reaction time. The reaction was vigorously stirred for about an hour at the autogenic pressure. The stirring was stopped, and the reaction was cooled to room temperature. The contents were allowed to settle and the organic layer (immiscible in the ionic liquid) was decanted off and washed with 0.1N KOH aqueous solution. The recovered oils were characterized with simulated distillation, bromine analysis, viscosity, viscosity indices, and pour and cloud points.

Table 3 below show the properties of the resulting oils of different 1-decene/isobutane ratios. All the reactions were run for approximately 1 hr at 50 degrees C. in the presence of 20 gm of ionic liquid catalyst.

TABLE 3

| SIMDIST TBP (WT %), °F. | $C_{10}=/$ iC4 = 0.8 | $C_{10}=/$ $iC_4 = 1$ | $C_{10}=/$ $iC_4 = 4$ | $C_{10}=/$ $iC_4 = 5.5$ | $C_{10}=/$ $iC_4 = 9$ |
|---|---|---|---|---|---|
| TBP @ 0.5 | 301 | 311 | 322 | 329 | 331 |
| TBP @ 5 | 340 | 382 | 539 | 605 | 611 |
| TBP @ 10 | 440 | 453 | 663 | 746 | 775 |
| TBP @ 20 | 612 | 683 | 792 | 836 | 896 |
| TBP @ 30 | 798 | 842 | 894 | 928 | 986 |
| TBP @ 40 | 931 | 970 | 963 | 999 | 1054 |
| TBP @ 50 | 1031 | 1041 | 1007 | 1059 | 1105 |
| TBP @ 60 | 1098 | 1099 | 1067 | 1107 | 1148 |
| TBP @ 70 | 1155 | 1154 | 1120 | 1154 | 1187 |
| TBP @ 80 | 1206 | 1205 | 1176 | 1200 | 1228 |
| TBP @ 90 | 1258 | 1260 | 1242 | 1252 | 1278 |
| TBP @ 95 | 1284 | 1290 | 1281 | 1282 | 1305 |
| TBP @ 99.5 | 1311 | 1326 | 1324 | 1313 | 1335 |

The data shown in Table 3 clearly indicate that the amount of isobutane added to the reaction does influence the boiling range of the produced oils. As shown in Table 3, there are more hydrocarbons in the lower boiling cuts at higher concentration of isobutane in the reaction. This indicates that more alkylation is taking part in the reaction when more isobutane is present. When more isobutane is present, 1-decene alkylation with $iC_4$ to make $C_{14}$ and decene dimer alkylation to make $C_{24}$ will be more prevalent than at lower concentrations of isobutane. Therefore, the degree of branching and oligomerization can be tailored by the choice of olefins, isoparaffins, olefin/isoparaffin ratios, contact time and the reaction conditions.

The alkylated oligomers will no longer take part in further oligomerizations due to "capping" off their olefinic sites, and the final oligomeric chain will be shorter perhaps than the normal oligomeric products but with more branching.

While the oligomerization pathway is the dominant mechanism, it is very clear that the alkylation of 1-decene and its oligomers with isobutane does take part in the chemistry.

Table 4 below compares some physical properties of the products obtained from the reactions of Table 3

TABLE 4

|  | C10=/ $iC_4 = 0.8$ | C10=/ $iC_4 = 1$ | C10=/ $iC_4 = 4$ | C10=/ $iC_4 = 5.5$ | C10=/ $iC_4 = 9$ |
|---|---|---|---|---|---|
| VI | 145 | 171 | 148 | 190 | 150 |
| Vis @ 100 | 9.84 | 7.507 | 9.73 | 7.27 | 11.14 |
| VIS @ 40 | 61.27 | 37.7 | 59.63 | 33.5 | 70.21 |
| Pour Point | −42 | −42 |  | −44 | −52 |
| Cloud Point | −63 | −64 |  | −69 | −28 |
| Bromine Number | 3.1 | 0.79 | 2.2 | 3.8 | 6.1 |

The oligomerization/alkylation run @ 1-decene/$iC_4$ ratio of 5.5 was repeated several times at the same feed ratios and conditions. The viscosity@100 in the repeated samples ranged from 6.9-11.2. The VI ranged from 156-172. All the repeated samples contained low boiling cuts (below 775 degrees F.) ranging from 10%-15%. The low boiling cut appears to influence the VI.

The Bromine Numbers shown in Table 4 are much less than usually observed for the 1-decene oligomerization in the absence of isobutane. The Bromine Number for 1-decene oligomerization in the absence of $iC_4$ is in the range of 7.5-7.9 based on the catalyst, contact time and catalyst amounts used in the oligomerization reaction.

As shown above, concurrent alkylation and oligomerization leads to oligomeric products with desirable Bromine Number, VI, viscosities, and pour and cloud points.

What is claimed is:

1. A process for making a distillate fuel component or lubricant component, comprising:
    performing concurrent alkylation and oligomerization in a common reaction zone by contacting a stream comprising one or more olefins and a stream comprising one or more isoparaffins, wherein an olefin to isoparaffin mole ratio in the common reaction zone is at least 0.5, with a catalyst comprising an acidic chloroaluminate ionic liquid that is a 1-butyl-pyridinium chloroaluminate in the presence of a Brönsted acid to form an alkylated oligomeric product having a Bromine Number of less than 4.

2. The process of claim 1 wherein said alkylated oligomeric product has a Bromine Number of less than 3.

3. The process of claim 1 wherein said alkylated oligomeric product is used as a fuel or a fuel blendstock.

4. The process of claim 1 wherein said alkylated oligomeric product is used as a lubricant base oil or a lubricant blendstock.

5. The process of claim 1 wherein said alkylated oligomeric product has a Bromine Number of less than 2.7.

6. A process for making a fuel or lubricant, comprising:
    passing a mixture comprising one or more olefins and an isoparaffin, wherein the mixture has a mole ratio of the one or more olefins to the isoparaffin of 0.5 or greater, to an oligomerization and alkylation zone, which is a common reaction zone, comprising an acidic chloroaluminate ionic liquid that is a 1-butyl pyridinium chloroaluminate, at oligomerization and alkylation conditions, to form an alkylated oligomeric product having a TBP@50 of at least 538 degrees C (1000 degrees F) by SIMDIST and a Bromine Number of less than 4.

7. The process of claim 6 wherein the oligomerization and alkylation zone further comprises a Brönsted acid.

8. The process of claim 6 wherein the isoparaffin is selected from the group consisting of isobutane, isopentane, and a mixture comprising isobutane and isopentane.

9. The process of claim 6 wherein the alkylated oligomeric product is subjected to hydrogenation to produce a low olefin lubricant base oil.

10. The process of claim 9 wherein said low olefin lubricant base oil has a Bromine Number of less than 0.2 by ASTM D 1159.

11. The process of claim 6 wherein the mixture comprising one or more olefins comprises at least one alpha olefin.

12. The process of claim 11 wherein the mixture comprising one or more olefins comprises at least 50 mole % of a single alpha olefin species.

13. The process of claim 11 wherein the mixture comprising one or more olefins consists of a mixture of alpha olefins.

14. The process of claim 11 wherein the alkylated oligomeric product is subjected to hydrogenation to form a low olefin content alkylated oligomer.

15. The process of claim 14 wherein the low olefin content alkylated oligomer has a Bromine Number of less than 0.2 as measured by ASTM D 1159.

16. A process for making a lubricant, comprising: performing concurrent alkylation and oligomerization in a common reaction zone by contacting a stream comprising one or more isoparaffins and having a mole ratio of an olefin to the one or more isoparaffins of 0.5 or greater with an acidic ionic liquid catalyst, that is a 1-butyl pyridinium chloroaluminate, and a Brönsted acid; wherein the lubricant has a viscosity@100 from 6.9 to 11.2.

17. The process of claim 16, wherein the lubricant additionally has a VI from 145 to 190.

18. The process of claim 16, wherein the lubricant additionally has a pour point of −42° C. or less.

* * * * *